US009210553B2

(12) United States Patent
Al et al.

(10) Patent No.: US 9,210,553 B2
(45) Date of Patent: Dec. 8, 2015

(54) MANAGEMENT METHOD AND APPARATUS FOR CLOSED SUBSCRIBER GROUP WHITE LIST

(75) Inventors: Ming Al, Beijing (CN); Guosheng Zhao, Beijing (CN)

(73) Assignee: CHINA ACADEMY OF TELECOMMUNICATIONS TECHNOLOGY, Beijing (CN)

( * ) Notice: Subject to any disclaimer, the term of this patent is extended or adjusted under 35 U.S.C. 154(b) by 223 days.

(21) Appl. No.: 13/638,445

(22) PCT Filed: Jun. 17, 2011

(86) PCT No.: PCT/CN2011/075844
§ 371 (c)(1),
(2), (4) Date: Sep. 28, 2012

(87) PCT Pub. No.: WO2011/157221
PCT Pub. Date: Dec. 22, 2011

(65) Prior Publication Data
US 2013/0029703 A1 Jan. 31, 2013

(30) Foreign Application Priority Data

Jun. 18, 2010 (CN) .......................... 2010 1 0209853

(51) Int. Cl.
*H04B 7/00* (2006.01)
*H04W 4/08* (2009.01)
(Continued)

(52) U.S. Cl.
CPC ............... *H04W 4/08* (2013.01); *H04L 63/101* (2013.01); *H04W 12/08* (2013.01); *H04W 8/186* (2013.01);
(Continued)

(58) Field of Classification Search
CPC ..... H04W 48/02; H04W 12/08; H04W 48/08; H04W 4/08; H04W 88/08; H04W 36/0038; H04W 48/20; H04W 8/186; H04L 63/101
See application file for complete search history.

(56) References Cited

U.S. PATENT DOCUMENTS

2002/0111180 A1 8/2002 Hogan et al.
2010/0051504 A1 3/2010 Lu et al.
(Continued)

FOREIGN PATENT DOCUMENTS

CN 101646248 A 2/2010
CN 101686437 A 3/2010
(Continued)

OTHER PUBLICATIONS

Motorola: "More Discussion on the Operator CSG list", 3GPP Draft; 3GPP Mobile Competence Centre ; 650, Route Des Lucioles ; F-06921 Sophia-Antipolis Cedex ; France, vol. SA WG1, no. SanFrancisco; Feb. 22, 2010, Feb. 10, 2010, pp. 1-2, XP050431614, [retrieved on Feb. 10, 2010].

(Continued)

*Primary Examiner* — Andrew Wendell
*Assistant Examiner* — Maryam Soltanzadeh
(74) *Attorney, Agent, or Firm* — Kilpatrick Townsend & Stockton LLP

(57) ABSTRACT

A management method and apparatus for a Closed Subscriber Group (CSG) white list are provided in the present invention, which can avoid the case that causes the CSG white list of a User Equipment (UE) to include a new Operator CSG List (OCL) and an old Allowed CSG List (ACL). The method includes the following steps: a User Equipment (UE) receives an updated Operator CSG List (OCL) or an Allowed CSG List (ACL) from a network side; according to the updated OCL or ACL, UE generates the CSG white list. With the present invention, when UE performs cells selection or handover according to the CSG white list which is provided to a non-access stratum by an access stratum as a basis for access control, the selected CSG identifier can not be refused by the network, the user experience can not be reduced, and unnecessary network signaling overhead can not be increased.

16 Claims, 4 Drawing Sheets

(51) Int. Cl.
    *H04L 29/06*     (2006.01)
    *H04W 12/08*     (2009.01)
    *H04W 24/00*     (2009.01)
    *H04W 28/06*     (2009.01)
    *H04W 36/08*     (2009.01)
    *H04W 48/16*     (2009.01)
    *H04W 48/20*     (2009.01)
    *H04W 8/18*     (2009.01)
    *H04W 48/02*     (2009.01)

(52) U.S. Cl.
    CPC ............... *H04W 24/00* (2013.01); *H04W 28/06* (2013.01); *H04W 36/08* (2013.01); *H04W 48/02* (2013.01); *H04W 48/16* (2013.01); *H04W 48/20* (2013.01)

(56) References Cited

U.S. PATENT DOCUMENTS

| | | | |
|---|---|---|---|
| 2010/0069069 A1* | 3/2010 | Lee et al. | 455/435.2 |
| 2011/0275385 A1* | 11/2011 | Escolar-Piedras et al. | 455/456.1 |
| 2012/0236828 A1* | 9/2012 | Hapsari et al. | 370/331 |
| 2013/0089076 A1* | 4/2013 | Olvera-Hernandez et al. | 370/332 |
| 2014/0146783 A1* | 5/2014 | Kim et al. | 370/329 |
| 2014/0220982 A1* | 8/2014 | Jung et al. | 455/437 |
| 2014/0274045 A1* | 9/2014 | Yu et al. | 455/434 |

FOREIGN PATENT DOCUMENTS

| | | |
|---|---|---|
| CN | 102088667 A | 6/2011 |
| EP | 2 117 261 A1 | 11/2009 |
| WO | 2010/075470 A1 | 1/2010 |

OTHER PUBLICATIONS

Gatt et al: "Correction to Allowed CSG List", 3GPP Mobile Competence Centre; 650, Route Des Lucioles ; F-06921 Sophia-Antipolis Cedex ; France, vol. RAN WG2, no. Jeju, Korea, Nov. 13, 2009, pp. 1-7, XP050604885, [retrieved on Nov. 13, 2009].

QUALCOMM Incorporated: "Discussion on the Interaction of the Allowed CSG list and Operator CSG list", 3GPP Draft; 3GPP Mobile Competence Centre; 650, Route Des Lucioles; F-06921 Sophia-Antipolis Cedex; France, vol. SA WG1 , Feb. 10, 2010, pp. 1-3, P050624529, [retrieved on Feb. 10, 2010].

Motorola: "Analysis and Conclusions on the CSG lists", 3GPP Draft; 3GPP Mobile Competence Centre ; 650, Route Des Lucioles; F-06921 Sophia-Antipolis Cedex; France, val. SA WG 1, Apr. 30, 2010, XP050624553, [retrieved on Apr. 30, 2010].

"3rd Generation Partnership Project; Technical Specification Group Services and System Aspects; Service requirements for Home Node B (HNB) and Home eNode 8 (HeNS) (Release 10)", 3GPP TS 22.220, 3GPP Mobile Competence Centre ; 650, Route Des Lucioles; F-06921 Sophia-Antipolis Cedex; France, No. V10.3.0, Jun. 16, 2010, pp. 1-25, XP050441778, [retrieved on Jun. 16, 2010].

European Search Report for EP 11795187, Sep. 20, 2013.

* cited by examiner

MANAGEMENT METHOD AND APPARATUS FOR CLOSED SUBSCRIBER GROUP WHITE LIST

This application is a Section 371 National Stage Application of International Application No. PCT/CN2011/075844, filed Jun. 17, 2011, designating the United States, and claims the benefit of Chinese Patent Application No. 201010209853.8, filed with the Chinese Patent Office on Jun. 18, 2010, entitled "Method and apparatus for managing white closed subscriber group list", both of which are hereby incorporated by reference in their entirety.

FIELD

The present invention relates to the field of mobile communications and particularly to a method and apparatus for managing a white closed subscriber group list.

BACKGROUND

For a User Equipment (UE), the $3^{rd}$ Generation Partnership Project (3GPP) defines only a Closed Subscriber Group (CSG) list in the Release 8 (R8), which is referred to as an Allowed CSG list or simply an ACL in this context.

An Operator CSG List (simply an OCL in this context) is introduced in the Release 9 (R9). An OCL may also be referred to as an Operator Controlled CSG List (OACL) in the R9.

For an allowed CSG list in the R8, a further need arises during a study of the Release 9 to allow a user to modify the ACL, and this ACL was referred to as a User CSG List (UCL) or a User Controlled CSG List (UACL) in the earlier specification of the Release 9 and is still referred to as an ACL in the latter specification of the R9 and the releases subsequent to the R9.

CSG subscription data, instead of the ACL and the OCL, is stored at the network side. CSG subscription data of a UE is stored in a Home Subscriber Server (HSS), a Mobility Management Entity (MME), a Serving GPRS Support Node (SGSN), a Mobile Switching Center (MSC) and other network nodes, which perform access control on the UE according to the CSG subscription data.

There is a further logic entity in the network, which is referred to as a CSG list server and updates the ACL and the OCL at the UE side in an Over-The-Air (OTA) or Open Mobile Alliance OMA DM Device Management (OMA DM) methods. This update method is characterized in updating the entire ACL or OCL of the UE.

In addition to the OTA and OMA DM methods, there is a further manual updating method (that is, in a Non Access Stratum (NAS) procedure) to update the ACL and the OCL at the UE. An underlying principle of the manual updating method lies in that the UE performs an NAS procedure in a specific CSG cell, and if the NAS procedure is accepted by the network, then a CSG ID of the CSG cell is added into the ACL (if the CSG ID is absent in the ACL), or if the network rejects the NAS procedure and gives a rejection reason of #25, then the CSG ID is deleted from the ACL (if the CSG ID is present in the ACL). The manual updating method (a method in an NAS procedure) can only update an ACL and can be performed only when the UE performs an NAS procedure in a CSG cell; and this method can not update the entire ACL concurrently.

In the UE, the NAS is responsible for maintaining and updating the OCL and the ACL and hereby generating a White CSG List (simply a WCL in this context) for use by an Access Stratum (AS). The AS selects a cell, prepares for a handover and other procedures according to the WCL.

The network may be configured not to use any ACL according to an operator policy.

As stated in the section of Closed Subscriber Group, the 3GPP Specification TS 22.220 5.3.2 for a demand of a CSG, the two lists, i.e., the ACL and the OCL, are maintained independently from each other. A change in the Operator CSG list shall not trigger the UE to modify the Allowed CSG list to reflect such change automatically.

A detailed definition of a method for integrating the ACL and the OCL into the WCL is absent in the existing specification. As current understanding of the specification, the UE regards both of CSGs in the ACL and the ACL as subscribed CSGs. Thus it can be considered that all of CSG IDs in the ACL and the OCL should be list into the WCL (that is, the ACL is combined with the OCL) and provided to the AS as an access control criterion in selecting a cell and in preparing for a handover, etc.

At the UE side, the existing specification considers such a scenario that when the UE performs an NAS procedure (for example, attachment, Tracking Area Update (TAU), Routing Area Update (RAU), and Service Request, etc.) in a specific CSG cell, a rejection reason of #25 is indicated to the UE when the UE is reject for an access to a non-subscribed CSG cell. The UE deletes a CSG ID of the CSG cell from the ACL upon reception of the rejection reason. If the CSG ID is also present in the OCL, then the UE may not include the CSG ID in the WCL under some condition dependent upon an implementation of the UE. Reference can be made to CSG Selection or Restriction, 3GPP 23.122 3.1A for details.

There is a further scenario where if the ACL is updated in the manual update method and the OCL is updated in the OTA or OMA DM method, then such a situation may arise that some CSG IDs are already absent in the OCL but these CSG IDs are still present in the ACL. A reason for this problem is that the network updates the OCL at the UE side through OMA DM or OTA but does not update the ACL as well and instead updates the ACL in an NAS procedure; or the NAS of the UE is going to provide the AS with the WCL before the network updates the ACL. Then the WCL of the UE may include the new OCL and the old ACL, and the NAS provides the AS with the WCL as an access control criterion. In this scenario, the UE selects a cell or performs a handover still according to the contents of the WCL (i.e., the old ACL and the new OCL), and once these CSG IDs are selected, a subsequent procedure will be rejected by the network, thus resulting the problems of degrading a user experience, increasing an unnecessary network signaling overhead, etc.

A drawback of the prior art lies in the absence of a technical solution to the foregoing two scenarios occurring.

SUMMARY

One aspect of the invention is to provide a method for managing a white closed subscriber group list, so as to address the problem in the prior art on management of a WCL.

An embodiment of the invention provides a method for managing a White Closed subscriber group List, WCL, which includes:

a User Equipment, UE, obtaining an Operator Closed subscriber group List, OCL, and/or an Allowed Closed subscriber group List, ACL, updated by the network side; and the UE generating the WCL from the updated OCL and/or ACL.

An embodiment of the invention provides another method for managing a White Closed subscriber group List, WCL, which includes:

the network side determining whether it is required to update an Allowed Closed subscriber group List, ACL, and/or an Operator Closed subscriber group List, OCL, at a User Equipment, UE; and if so, then the network side updating the ACL and the OCL at the UE concurrently or in the same update operation process.

An embodiment of the invention provides a user equipment including:

a receiving module configured to receive an updated Operator Closed subscriber group List, OCL, and/or an Allowed Closed subscriber group List, ACL, from the network side; and a generating module configured to generate a White Closed subscriber group List, WCL, from the updated OCL and/or ACL.

An embodiment of the invention provides a network side device including:

a determining module configured to determine whether it is required to update an Allowed Closed subscriber group List, ACL, or an Operator Closed subscriber group List, OCL, at a User Equipment, UE; and an updating module configured to update the ACL and the OCL at the UE concurrently or in the same updating process when updating is required.

Advantageous effects of embodiments of the invention are as follows.

Since the network side also updates the ACL while updating the OCL at the UE side through OMA DM or OTA instead of updating the ACL in an NAS procedure, such a situation can be avoided that some CSG IDs are already absent in the OCL but these CSG IDs are still present in the ACL, which might otherwise occur when the ACL is updated in a manual updating method and the OCL is updated in an OTA or OMA DM method. Furthermore such a situation can also be avoided that a WCL of the UE includes the new OCL and the old ACL, therefore, when the UE selects a cell or performs a handover according to the WCL provided to an AS from an NAS as an access control criterion, a selected CSG ID will not be rejected by the network, a user experience will not be degraded and no unnecessary network signaling overhead will be increased.

DETAILED DESCRIPTION OF THE EMBODIMENTS

Embodiments of the invention will be described below with reference to the drawings.

Figure 1:
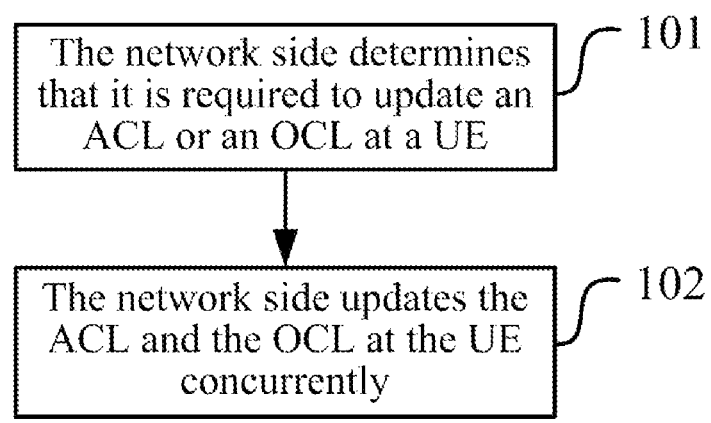
FIG. 1 is a schematic flow chart of performing a method for managing a WCL at the network side according to an embodiment of the invention.

FIG. 1 is a schematic flow chart of performing a method for managing a WCL at the network side, and as illustrated, a WCL can be managed at the network side in the following operations 101 and 102.

Operation 101. The network side determines that it is required to update an ACL or an OCL at a UE; and Operation 102. The network side updates the ACL and the OCL at the UE concurrently.

In an implementation, the network side may update the ACL and the OCL at the UE concurrently in an OMA DM method or in an OTA method.

Particularly if the network is going to update the ACL or the OCL at the UE, then the network should update the ACL and the OCL concurrently or update the ACL and the OCL in the same update operation process. This solution is applicable to a situation where the network adopts OMA DM or OTA.

For example, the network side also updates the ACL while deleting one or more list entries in the OCL so as to avoid the list entry or entries deleted in the OCL from being present in the ACL, where the table entry is a CSG ID.

Since the network side also updates the ACL while updating the OCL at the UE side through OMA DM or OTA instead of updating the ACL in an NAS procedure, such a situation may be avoided that some CSG IDs are already absent in the OCL but these CSG IDs are still present in the ACL, which might otherwise occur when the ACL is updated in a manual updating method and the OCL is updated in an OTA or OMA DM method. Furthermore such a situation may also be avoided that a WCL of the UE includes the new OCL and the old ACL. Therefore, when the UE selects a cell or performs a handover according to the WCL provided to an AS from an NAS as an access control criterion, a selected CSG ID will not be rejected by the network, a user experience will not be degraded and no unnecessary network signaling overhead will be increased.

A solution to management of a WCL at the UE side will be described below. It is intended to address at least the following issues 1) and 2) which have not been set forth in the existing specification:

1) when a UE generates a WCL; and
2) how an NAS provides an AS with the WCL and when it provides the AS with the WCL.

Figure 2:
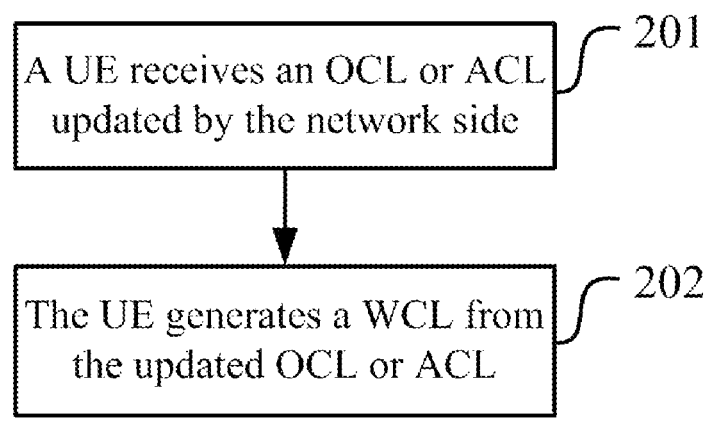
FIG. 2 is a schematic flow chart of performing a method for managing a WCL at the UE side according to an embodiment of the invention.

FIG. 2 is a schematic flow chart of performing a method for managing a WCL at the UE side, and as illustrated, a WCL can be managed at the UE side in the following operations 201 and 202.

Operation 201. A UE receives an updated OCL and/or ACL from the network side; and Operation 202. The UE generates a WCL from the updated OCL and/or ACL.

As for the UE generating the WCL from the updated OCL and/or ACL, a description will be given primarily to two situations, in one of which the network side updates the OCL, and in the other of which the network side updates the ACL, and in a further situation, the network side updates the OCL and the ACL concurrently or in the same update operation process.

As to the time when the UE generates the WCL from the updated OCL and/or ACL, the WCL may be generated when the AS of the UE needs to access the WCL, or the WCL may be generated immediately after the OCL and/or the ACL is/are updated. A description will be given below.

I. In the situation that the network side updates the OCL, the UE generates the WCL from the updated OCL and/or ACL by:

putting a CSG ID or IDs belonging to both the ACL and the OCL into the WCL;

not putting any CSGI ID belonging to the ACL but not the OCL into the WCL; and putting or not putting a CSG ID or IDs belonging to the OCL but not the ACL into the WCL.

In an implementation, when the network side updates the OCL of the UE in the OMA DM and OTA methods, the UE side may generate the WCL as follows.

The UE puts those CSG IDs present in the ACL and also in the OCL into the WCL and does not put any CSG ID present in the ACL but absent in the OCL into the WCL.

If a specific CSG ID is absent in the ACL but present in the OCL, then the CSG ID may be added into the WCL or may not be added into the WCL (even if the CSG ID is absent in the WCL).

A further description will be given below with embodiments.

First Embodiment

In this embodiment, the WCL is generated immediately after the OCL and/or the ACL is/are updated.

Assumed the NAS of the UE maintains the WCL and updates the WCL immediately when the OCL or the ACL is updated. The AS may search for the WCL directly when it needs to access the WCL. In an embodiment, the UE updates the WCL immediately when the network side updates the OCL of the UE in the OMA DM and OTA methods.

Assumed information of the three lists of the UE is as follows before the OCL of the UE is updated in the OMA DM and OTA methods:

The WCL includes IDs of a CSG, which are A, B, C, D and E;

The ACL includes IDs of a CSG, which are A, B, C, D and E; and

The OCL includes IDs of a CSG, which are A, B, C, D and E.

After the OCL is updated, the OCL includes IDs of the CSG, which are A, B, C and F (F is newly added). Then the UE shall update the WCL. A specific update rule is as follows: if a specific CSG ID is present in the WCL but absent in the OCL, then the CSG ID is deleted from the WCL; and if a specific CSG ID is absent in the ACL but present in the OCL, then the CSG ID may (or may not) be added into the WCL (even if the CSG ID is absent in the ACL). Under this rule, the updated WCL includes CSG IDs of A, B, C and F or of A, B and C.

II. In the situation that the network side updates the ACL, the UE generates the WCL from the updated OCL and/or ACL by:

putting a CSG ID or IDs belonging to both the ACL and the OCL into the WCL;

not putting any CSG ID belonging to the OCL but not the ACL into the WCL; and putting or not putting a CSG ID or IDs belonging to the ACL but not the OCL into the WCL.

In an implementation, when the network side updates the ACL of the UE in the OMA DM and OTA methods, the UE side may generate the WCL as follows.

The UE puts those CSG IDs present in the ACL and also in the OCL into the WCL and does not put any CSG ID present only in the OCL but absent in the ACL into the WCL.

If a specific CSG ID is absent in the OCL but present in the ACL, then the CSG ID may be added into the WCL or may not be added into the WCL (even if the CSG ID is absent in the WCL).

For a specific implementation, reference can be made to the first embodiment.

As to the time when the UE generates the WCL from the updated OCL or ACL, the WCL may be generated when the AS of the UE needs to access the WCL, or the WCL may be generated immediately after the OCL or the ACL is updated, for the latter of which, reference can be made to the first embodiment, and the former of which will be described below.

In an implementation, the following may further be included.

The UE records the time when the network side updates the OCL and the time when the network side updates the ACL; and When the AS of the UE needs to access the WCL, the WCL is generated in such a way that the ACL or the OCL with a closer update time to a current time is selected to generate the WCL.

Particularly the WCL may be generated on demand based upon the latest update time.

Second Embodiment

The UE records the time when the OCL is updated.

If the ACL is also updated in the OAM DM and OTA methods, then the time when the ACL is updated is recorded.

When the AS of the UE needs to access the WCL, for example, when the NAS instructs the AS to select a cell, the NAS needs to generate the WCL according to the ACL and the OCL. The NAS may generate the WCL under such a rule as follows:

CSG IDs required to generate the WCL are finally determined from the list among the OCL and the ACL with the latest update time according to their update times.

For example, the ACL is updated at the time of 2010-5-4: 21:00 and includes CSG IDs of A, B and C; and The OCL is updated at the time of 2010-5-4:23:00 and includes CSG IDs of A, B, C, D and E.

Then under the foregoing rule, the generated WCL includes CSG IDs of A, B, C, D and E.

In an implementation, in view of a potentially occurring NAS procedure resulting in updating of the ACL, the following may also be included.

The UE determines whether there is an NAS procedure resulting in updating of the ACL; and If so, then the UE records the time when the ACL is updated in the NAS procedure.

Alike when the AS of the UE needs to access the WCL, the WCL is generated in such a way that the ACL or the OCL with a closer update time to a current time is selected to generate the WCL.

Embodiment 3

If an NAS procedure occurs resulting in updating of the ACL, for example, by deleting a specific CSG ID from the ACL or adding a specific CSG ID into the ACL, then for the CSG ID, an operation time for the CSG ID is recorded. When the WCL is generated on demand, whether to include the CSG ID into the WCL is determined from the operation time. For example:

At 00:00, May 4, 2010, the lists of the NAS is as follows:

The ACL includes IDs of a CSG which are A, B, C, D and E, and the entire list is updated at the time of 00:00, May 3, 2010.

There is a list of ACL:: $\{A, B, C, D, E\}_{T=201005030000}$.

The OCL includes IDs of a CSG which are A, B, C, D and E, and it is updated at the time of 01:00, May 3, 2010.

There is a list of OCL:: $\{A, B, C, D, E\}_{T=201005030100}$.

An NAS procedure results in adding of a CSG ID of 'F' into the ACL at the time of 02:00, May 3, 2010.

There is a list of ACL:: $\{A, B, C, D, E, F_{T=201005030200}\}_{T=201005030000}$.

Again an NAS procedure results in deleting of the CSG ID of 'E' from the ACL at the time of 03:00, May 3, 2010.

There is a list of ACL:: $\{A, B, C, D, -E_{T=201005030300}, F_{T=201005030200}\}_{T=201005030000}$.

Where '-E' represents an operation of deleting the list element 'E'.

At 04:00, May 3, 2010, the NAS needs to generate the WCL, the update time of CSG IDs of A, B, C and D in the ACL is 01:00, May 3, 2010, the update time of CSG ID of F in the ACL is 02:00, May 3, 2010, and the update time of CSG ID of -E is 03:00, May 3, 2010. As a final result, F should be newly added into the WCL and E should not be added into the WCL.

A list of WCL may be obtained as WCL:: $\{A, B, C, D, F\}_{T=201005030400}$, where T=201005030400 characterizes the final generation time of the WCL.

Thus there are four relevant time tags:
The final generation time of the OCL: $T_{OCL}$;
The final generation time of the ACL: $T_{ACL}$;
The final generation time of the WCL: $T_{WCL}$; and
The final generation time of a specific element in the ACL: $T_X$.

When it is required later to combine the OCL and the ACL into the WCL, the WCL will be updated and generated only if "$T_{OCL}$ or $T_{ACL}$ or $T_X$ is later than $T_{WCL}$" holds so as to ensure logic correction and reduce unnecessary operations.

Based upon the same inventive idea, an embodiment of the invention further provides a user equipment and a network side device, and since the equipment and the device address the problem under a similar principle to the method for managing a WCL, reference can be made to the implementation of the method for an implementation of the equipment and the device, and a repeated description will be omitted.

When the network side updates the OCL and the ACL concurrently or in the same update operation process, the UE receives the updated OCL and ACL subsequently in two messages in a very short period of time and then generates the WCL from the updated OCL and ACL.

Figure 3:
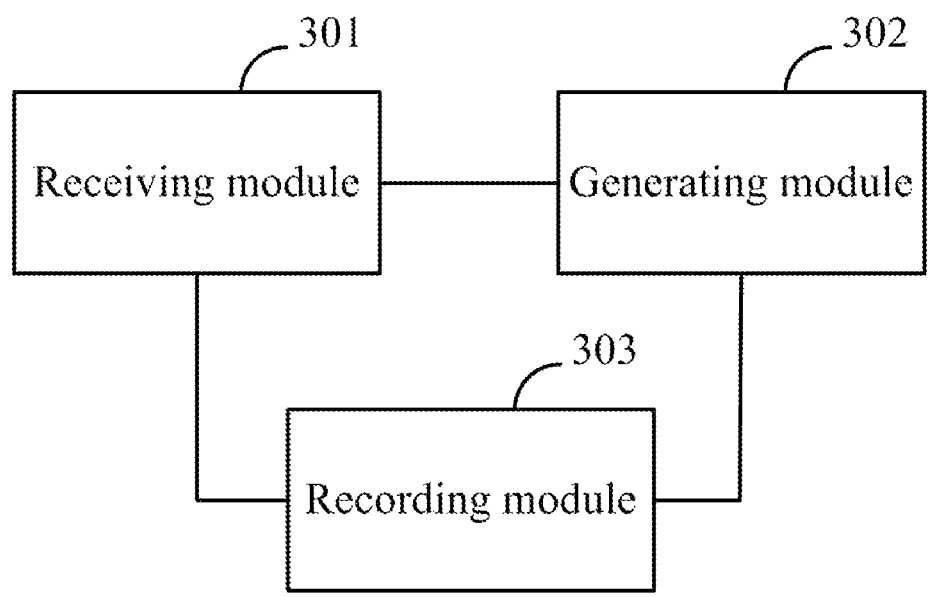
FIG. 3 is a schematic diagram of the structure of a user equipment according to an embodiment of the invention.

FIG. 3 is a schematic diagram of the structure of a user equipment, and as illustrated, the UE may include:
a receiving module 301 configured to receive an updated OCL and/or ACL from the network side; and
a generating module 302 configured to generate a WCL from the updated OCL and/or ACL.

In an implementation, the generating module may include a first generating unit and/or a second generating unit, where:
The first generating unit is configured, when the network side updates the OCL, to put a CSG ID or IDs belonging to both the ACL and the OCL into the WCL, not to put a CSG ID or IDs belonging to the ACL but not the OCL into the WCL, and to put or not to put a CSG ID or IDs belonging to the OCL but not the ACL into the WCL; and
The second generating unit is configured, when the network side updates the ACL, to put a CSG ID or IDs belonging to both the ACL and the OCL into the WCL, not to put a CSG ID or IDs belonging to the OCL but not the ACL into the WCL, and to put or not to put a CSG ID or IDs belonging to the ACL but not the OCL into the WCL.

In an implementation, the generating module generates the WCL from the updated OCL or ACL by generating the WCL when an AS of the UE needs to access the WCL or generating the WCL immediately after the OCL or the ACL is updated.

In an implementation, the UE may further include:
a recording module 303 configured to record the time when the network side updates the OCL and the time when it updates the ACL.

The generating module generates the WCL from the updated OCL or ACL by selecting the ACL and/or the OCL with a closer update time to a current time to generate the WCL.

In an implementation, the recording module may further be configured to determine whether there is an NAS procedure resulting in updating of the ACL, and if so, then record the time when the ACL is updated in the NAS procedure.

Alike the generating module generates the WCL from the updated OCL or ACL by selecting the ACL and/or the OCL with a closer update time to a current time to generate the WCL.

Figure 4:
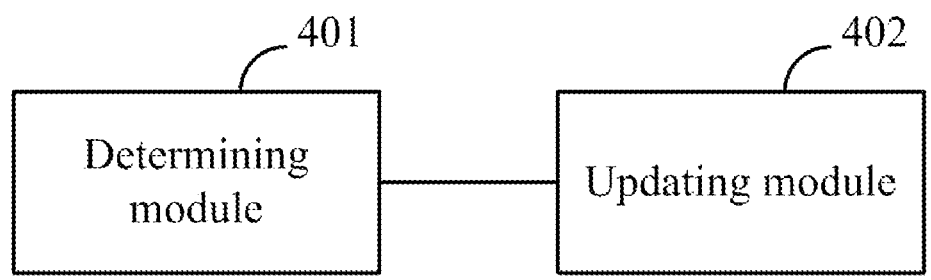
FIG. 4 is a schematic diagram of the structure of a network side device according to an embodiment of the invention.

FIG. 4 is a schematic diagram of the structure of a network side device, and as illustrated, the network side device may include:
a determining module 401 configured to determine whether it is required to update an ACL or an OCL at a UE; and
an updating module 402 configured to update the ACL and the OCL at the UE concurrently or in the same updating process when updating is required.

In an implementation, the updating module may further be configured to update the ACL and the OCL at the UE concurrently or in the same updating process in an OMA DM method or an OTA method.

For example, when the determining module 401 determines that it is required to delete one or more list entries in the OCL (that is, delete one or more CSG IDs in the OCL), the updating module 402 updates the ACL and the OCL at the UE concurrently or updates the ACL and the OCL at the UE in the same update operation process so as to avoid the list entry or entries deleted in the OCL from being still stored in the ACL.

For the convenience of a description, the respective components of the foregoing devices have been described respectively by functionally dividing them into respective modules or units. Of course the functions of the respective modules or units can be performed in the same one or a plurality of items of software or hardware to put the invention into practice.

Those skilled in the art shall appreciate that the embodiments of the invention can be embodied as a method, a system or a computer program product. Therefore the invention can be embodied in the form of an all-hardware embodiment, an all-software embodiment or an embodiment of software and hardware in combination. Furthermore the invention can be embodied in the form of a computer program product embodied in one or more computer useable storage mediums (including but not limited to a disk memory, a CD-ROM, an optical memory, etc.) in which computer useable program codes are contained.

The invention has been described in a flow chart and/or a block diagram of the method, the device (system) and the computer program product according to the embodiments of the invention. It shall be appreciated that respective flows and/or blocks in the flow chart and/or the block diagram and combinations of the flows and/or the blocks in the flow chart and/or the block diagram can be embodied in computer program instructions. These computer program instructions can be loaded onto a general-purpose computer, a specific-purpose computer, an embedded processor or a processor of another programmable data processing device to produce a machine so that the instructions executed on the computer or the processor of the other programmable data processing device create means for performing the functions specified in the flow(s) of the flow chart and/or the block(s) of the block diagram.

These computer program instructions can also be stored into a computer readable memory capable of directing the computer or the other programmable data processing device to operate in a specific manner so that the instructions stored in the computer readable memory create an article of manufacture including instruction means which perform the functions specified in the flow(s) of the flow chart and/or the block(s) of the block diagram.

These computer program instructions can also be loaded onto the computer or the other programmable data processing device so that a series of operational steps are performed on the computer or the other programmable data processing device to create a computer implemented process so that the instructions executed on the computer or the other programmable device provide steps for performing the functions specified in the flow(s) of the flow chart and/or the block(s) of the block diagram.

Although the preferred embodiments of the invention have been described, those skilled in the art benefiting from the underlying inventive concept can make additional modifications and variations to these embodiments. Therefore the appended claims are intended to be construed as encompassing the preferred embodiments as well as all the modifications and variations falling into the scope of the invention.

The invention claimed is:

1. A method for managing a White Closed subscriber group List, WCL, wherein the method comprises:
   a User Equipment, UE, obtaining an Operator Closed subscriber group List, OCL, and/or an Allowed Closed subscriber group List, ACL, updated by a network side; and
   the UE generating the WCL from the updated OCL and/or ACL,
   wherein when the UE obtains the OCL updated by the network side, the UE generating the WCL from the updated OCL which comprises:
       the UE putting a Closed Subscriber Group Identifier, CSG ID, or IDs belonging to both the ACL and the updated OCL into the WCL in which a CSG ID or IDs belonging to the ACL but not the updated OCL is/are not included; and
   when the UE obtains the ACL updated by the network side, the UE generating the WCL from the updated ACL which comprises:
       the UE putting a Closed Subscriber Group Identifier, CSG ID, or IDs belonging to both the OCL and the updated ACL into the WCL in which a CSG ID or IDs belonging to the OCL but not the updated ACL is/are not included.

2. The method according to claim 1, wherein the UE generates the WCL from the updated OCL and/or ACL when an Access Stratum, AS, of the UE needs to access the WCL or after the OCL and/or the ACL is updated.

3. The method according to claim 2, further comprising:
   the UE recording the time when the network side updates the OCL and the time when the network side updates the ACL; and
   if the UE generates the WCL from the updated OCL and/or ACL when the Access Stratum, AS, of the UE needs to access the WCL, the generated WCL is a WCL generated from the ACL or the OCL with a closer update time to a current time.

4. The method according to claim 3, further comprising:
   the UE recording the time when the ACL is updated in a Non Access Stratum, NAS, procedure resulting in updating of the ACL when presence of the NAS procedure is determined.

5. A method for managing a White Closed subscriber group List, WCL, wherein the method comprises:
   the network side determining whether it is required to update an Allowed Closed subscriber group List, ACL, or an Operator Closed subscriber group List, OCL, at a User Equipment, UE; and
   if so, then the network side updating the ACL and the OCL at the UE concurrently or in the same update operation process.

6. The method according to claim 5, wherein the network side determining whether it is required to update the ACL or the OCL at the UE comprises:
   the network side determining whether it is required to delete one or more list entries in the OCL; and
   the network side updating the ACL and the OCL at the UE concurrently or in the same update operation process comprises:
   the network side updating the ACL and the OCL at the UE concurrently or in the same update operation process upon determining that it is required to delete one or more list entries in the OCL.

7. The method according to claim 5, wherein the network side updates the ACL and the OCL at the UE concurrently or in the same update operation process in an Open Mobile Alliance Device Management, OMA DM, method or an Over The Air, OTA, method.

8. A user equipment, comprising:
   a receiving module configured to receive an updated Operator Closed subscriber group List, OCL, and/or Allowed Closed subscriber group List, ACL, from a network side; and
   a generating module configured to generate a White Closed subscriber group List, WCL, from the updated OCL and/or ACL,
   wherein the generating module comprises a first generating unit and/or a second generating unit, wherein:
   the first generating unit is configured, when the receiving module receives the updated OCL from the network side, to put a CSG ID or IDs belonging to both the ACL and the OCL into the WCL in which a CSG ID or IDs belonging to the ACL but not the OCL is/are not included; and
   the second generating unit is configured, when the receiving module receives the updated ACL from the network side, to put a CSG ID or IDs belonging to both the ACL and the OCL into the WCL in which a CSG ID or IDs belonging to the OCL but not the ACL is/are not included.

9. The user equipment according to claim 8, wherein the generating module generates the WCL from the updated OCL and/or ACL when an Access Stratum, AS, of the user equipment needs to access the WCL or the generating module generates the WCL after the OCL and/or the ACL is updated.

10. The user equipment according to claim 9, wherein the user equipment further comprises: a recording module configured to record the time when the network side updates the OCL and the time when the network side updates the ACL; and
   when the generating module generates the WCL from the updated OCL and/or ACL, the generated WCL is a WCL generated from the ACL and/or the OCL with a closer update time to a current time.

11. The user equipment according to claim 10, wherein the recording module is further configured to record the time when the ACL is updated in a Non Access Stratum, NAS, procedure resulting in updating of the ACL when presence of the NAS procedure is determined.

12. A network side device, comprising:
   a determining module configured to determine whether it is required to update an Allowed Closed subscriber group List, ACL, or an Operator Closed subscriber group List, OCL, at a User Equipment, UE; and an updating module configured to update the ACL and the OCL at the UE concurrently or in the same updating process when updating is required.

13. The device according to claim 12, wherein:
the determining module determines whether it is required to delete one or more list entries in the OCL; and
when the determining module determines that it is required to delete one or more list entries in the OCL, the updating module updates the ACL and the OCL at the UE concurrently or in the same update operation process.

14. The device according to claim 12, wherein the updating module updates the ACL and the OCL at the UE concurrently or in the same update operation process in an Open Mobile Alliance Device Management, OMA DM, method or an Over The Air, OTA, method.

15. The method according to claim 1, wherein the UE generates the WCL from the updated OCL and/or ACL when an Access Stratum, AS, of the UE needs to access the WCL or after the OCL and/or the ACL is updated.

16. The user equipment according to claim 8, wherein the generating module generates the WCL from the updated OCL and/or ACL when an Access Stratum, AS, of the user equipment needs to access the WCL or the generating module generates the WCL after the OCL and/or the ACL is updated.

* * * * *